(12) United States Patent
Bruland

(10) Patent No.: US 9,821,486 B2
(45) Date of Patent: Nov. 21, 2017

(54) INTEGRATED LAMELLAE EXTRACTION STATION

(71) Applicant: FEI Company, Hillsboro, OR (US)

(72) Inventor: Kelly Bruland, Portland, OR (US)

(73) Assignee: FEI Company, Hillsboro, OR (US)

( * ) Notice: Subject to any disclaimer, the term of this patent is extended or adjusted under 35 U.S.C. 154(b) by 765 days.

(21) Appl. No.: 14/066,782

(22) Filed: Oct. 30, 2013

(65) Prior Publication Data

US 2015/0114193 A1    Apr. 30, 2015

(51) Int. Cl.
*B23K 26/00* (2014.01)
*G01N 1/32* (2006.01)
*B26D 7/18* (2006.01)
*G01N 1/28* (2006.01)

(52) U.S. Cl.
CPC .............. *B26D 7/18* (2013.01); *G01N 1/286* (2013.01); *G01N 1/32* (2013.01); *H01J 2237/204* (2013.01); *H01J 2237/208* (2013.01); *H01J 2237/31745* (2013.01); *Y10T 83/0467* (2015.04); *Y10T 83/2074* (2015.04)

(58) Field of Classification Search
CPC .. H01J 37/28; H01J 37/20; H01J 37/26; H01J 37/31; H01J 37/285; H01J 2237/2812; H01J 2237/31745; H01J 2237/202; H01J 2237/2802; H01J 2237/3114; G01N 1/28; G01N 1/32; G01N 2001/2886; G01N 2001/2873; B23K 15/006; B23K 26/0066
See application file for complete search history.

(56) References Cited

U.S. PATENT DOCUMENTS

| | | | |
|---|---|---|---|
| 6,268,608 B1 | 7/2001 | Chandler | |
| 8,357,913 B2 | 1/2013 | Agorio et al. | |
| 8,455,821 B2 | 6/2013 | Arjavac et al. | |
| 2005/0006600 A1* | 1/2005 | Shichi | B23K 15/0006 250/492.21 |
| 2008/0173815 A1* | 7/2008 | Nakasuji | G01N 23/225 250/310 |

(Continued)

FOREIGN PATENT DOCUMENTS

| | | |
|---|---|---|
| EP | 1512956 A2 | 3/2005 |
| WO | 2008051880 A2 | 5/2008 |

*Primary Examiner* — Brian Jennison
(74) *Attorney, Agent, or Firm* — Scheinberg & Associates, P.C.; Michael O. Scheinberg; John B. Kelly

(57) ABSTRACT

An integrated station for extracting specimens suitable for viewing by a transmission electron microscope from a patterned semiconductor wafer, including a wafer cassette holder; a wafer transfer device; a nanomachining device, including a scanning electron microscope and a focused ion beam, a vacuum load lock and an operator control device, and wherein the operator control device notes locations of created lamellae; a plucker device; a control computer, adapted to control the wafer transfer device and the plucker device, commanding the plucker device to remover lamellae at the locations noted by the operator control device; and a user monitor and data input device, communicatively coupled to the computer. The wafer transfer device can transfer wafers from the wafer cassette holder to the vacuum load lock; from the vacuum load lock to the plucker device and from the plucker device to the wafer cassette holder.

22 Claims, 5 Drawing Sheets

(56) References Cited

U.S. PATENT DOCUMENTS

| | | | |
|---|---|---|---|
| 2010/0305747 A1* | 12/2010 | Agorio | G01N 1/286 700/213 |
| 2012/0119084 A1 | 5/2012 | Shaapur et al. | |
| 2013/0328246 A1 | 12/2013 | Wells et al. | |

* cited by examiner

INTEGRATED LAMELLAE EXTRACTION STATION

TECHNICAL FIELD OF THE INVENTION

The present invention relates to semiconductor wafer testing and analysis. More specifically, the present invention relates to the extraction of specimens (referred to below as "lamellae") that are less than 100 nm thick from a semiconductor wafer, for viewing on a Transmission Electron Microscope or Scanning Transmission Electron Microscope (collectively S/TEM).

BACKGROUND OF THE INVENTION

The manufacturing of semiconductor integrated circuits starts with a semiconductor wafer, which is typically a silicon disk, which is patterned by way of photolithography, before being cut apart into dies, each one constituting an individual integrated circuit, which is then packaged for sale. After the patterning, it is frequently desirable to examine sections of the wafer very closely, to determine the process results. Due to the nanometric dimensions of the features this examination is often performed using S/TEMs, which are limited to the examination of specimens having a thickness of less than 100 nm. As a result, it is necessary to extract lamellae from the wafer, for imaging by the S/TEM.

This extraction starts with a nanomachining device which may be as shown in simplified form in FIG. 1 and disclosed in greater detail in U.S. Pat. No. 6,268,608, which is incorporated by reference as if fully set forth herein. Nanomachining device 10 includes a scanning electron microscope (SEM) 12 which is used for viewing extraction sites and a focused ion beam (FIB) 14, which is used to remove wafer material, thereby defining lamellae. A gas injection device 16 may be used in conjunction with FIB 14 or SEM 12, to deposit a selected material. The machining takes place in a vacuum chamber 18. A vacuum load lock 20 facilitates introducing and removing wafers into sample vacuum chamber without opening. Alternatively, a nanomachining device may include a FIB, used for both imaging and machining, but no SEM.

In some instances, the nanomachining device 10 is used to finish the extraction (in situ extraction), typically with direct human control of the FIB 14, which is used to completely separate the lamellae from a wafer 15, and a very fine shaft 22, controlled by a micromanipulator 17, which is used to pick up and deposit the lamellae from the wafer 15 supported on machining stage 23 onto a sample holder referred to as a TEM grid. In some instances of in situ extraction, the lamella is attached to the fine shaft 22 by ion beam-induced deposition and transported to a toothed grid, to which the lamella is attached, again by ion beam-induced deposition, and then the connection between the lamella and the fine shaft is severed.

To introduce a new wafer into vacuum chamber 18, a wafer movement device 24 includes a robot arm 26 for moving wafers into the vacuum lock 20 from a wafer cassette holder 28. An air filtering system 30, maintains low particulate levels in wafer movement device 24, thereby introducing fewer contaminants into vacuum chamber 18, through lock 20.

A suite of support and control equipment 32 interfaces with SEM 12, FIB 14, gas injection device 16 and the shaft 22. Equipment suite 32 is in turn controlled by a computer 34, which feeds and responds to a user monitor and control device 36, permitting a human user to control the process.

The vacuum lock 20, wafer movement device 24 including the robot arm 26, the wafer cassette holder 28, the air filtering system 30 and the user monitor and control device 36 are all considered to be part of the front end 40 of device 10. The front end must be carefully constructed to interface correctly with the vacuum chamber 18 and the equipment inside the vacuum chamber 18. For example, because the SEM 12 and FIB 14 are extremely sensitive to vibrations, chamber 18 floats on four pneumatic cushions 42, (two shown) to minimize the vibration of chamber 18. When arm 26 must load a wafer into or remove a wafer from vacuum lock 20 (which is designed to hold two wafers, to ease flow of wafers into and out of chamber 18), it is necessary that the vacuum lock 20, which is rigidly attached to the walls of chamber 18, be aligned with the front end 40. To do this a special pneumatic or hydraulic cylinder 44 is provided, to move lock into this alignment. Accordingly, communications must synchronize this alignment process and the transfer of wafers.

This in situ lamella removal technique requires more human time and more time at the nanomachining device, than the ex situ technique that will be described below, thereby reducing throughput of this device, which is highly undesirable for a costly, high-throughput device. Nanomachining devices that are currently in the design phase should have a throughput of about 10 to 20 minutes per lamellae, with the extraction of the lamellae potentially adding another 3 to 5 minutes per lamellae. Accordingly, being able to perform the lamellae extraction outside of the nanomachining device (ex situ extraction) could significantly increase throughput.

An ex situ plucker 110 is shown in simplified form in FIG. 2 and described in greater detail in U.S. Pat. No. 8,357,913, which is incorporated by reference as if fully set forth herein. Referring to FIG. 2, a stage 112 supports a wafer (not shown), and an illumination source 114, utilizing a fiber optic bundle 116 provides oblique illumination. An optical microscope 118 permits magnified viewing, and a vacuum shaft 120, controlled by a micromanipulator 122, is used to pluck the lamellae, in a process described below in more detail. A suite of control and support equipment 124 serves and controls the optical microscope 118, illumination source 114 and vacuum shaft 120. In turn a computer 126, which includes a data input assembly, controls suite 124, and a user monitor and control system 128, is fed by and controls computer 126. In one embodiment, the data input assembly of the computer 126 includes additional data ports, such as an Ethernet connection and USB ports. Also, a wafer movement device 130 uses a robot arm 132 to move wafers from a wafer cassette holder 134 to the stage 112. Finally an air filtering system 140, maintains air cleanness in station 110.

Referring to FIG. 3, which shows a section of wafer 210 that has been nanomachined to create a lamella 212, in preparation for sending the wafer to an ex situ plucker, such as device 110. Each lamella 212, including S/TEM viewing area 214, which is thinned sufficiently to be imaged by a S/TEM, is prepared in the nanomachining device 10, and left connected to the wafer by a pair of wafer-material tabs 216, defined in part by upwardly extending side cuts 218, so that the position of each lamellae remains fixed, prior to plucking.

Referring to FIGS. 4 and 5, the ex situ plucker 110 frees the lamella 212 though the use of a vacuum shaft 220 guided to the known position of each lamella, at a preset angle 224, adapted to provide optimum engagement with the known orientation of the lamella 212. The vacuum shaft 220, is moved into a position 220', contacting the lamella 212 and is used to push and pull the lamella 212 until the tabs 216 (FIG. 3) break and then lifts it and places it into a lamella holding grid (not shown), for transport to a S/TEM device for imaging. Unfortunately, the expense of ex situ pluckers, plus the added complication of having to move the wafer and data from nanomachining device to ex situ plucker have limited the desirability of this solution.

SUMMARY OF THE INVENTION

An object of the invention is to provide a higher throughput device for fully extracting lamellae from a wafer. One preferred embodiment of the present invention, therefore, is a fully integrated lamellae extraction station to create lamellae. The station includes both a nanomachining device, and a lamellae plucker to remove the lamellae from the wafer and place them in a grid for transport to a S/TEM. In addition, one or more wafer cassette holders permit wafers to be introduced into the station and removed from the station and a wafer transfer device moves wafers from the wafer cassette holder(s) to the nanomachining device, from there, to the plucker and then back to the wafer cassette holder(s). Another preferred embodiment is the method of using this station to create lamellae, by using the wafer transfer device to move a wafer from wafer cassette holder to nanomachining station, machining a lamellae, and then using the wafer transfer device to transfer the wafer to the plucker station which plucks the lamellae, and places it in a holding device. Finally, the wafer is returned to a holding station. A third embodiment is the computer readable memory media holding a computer program to perform this method.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
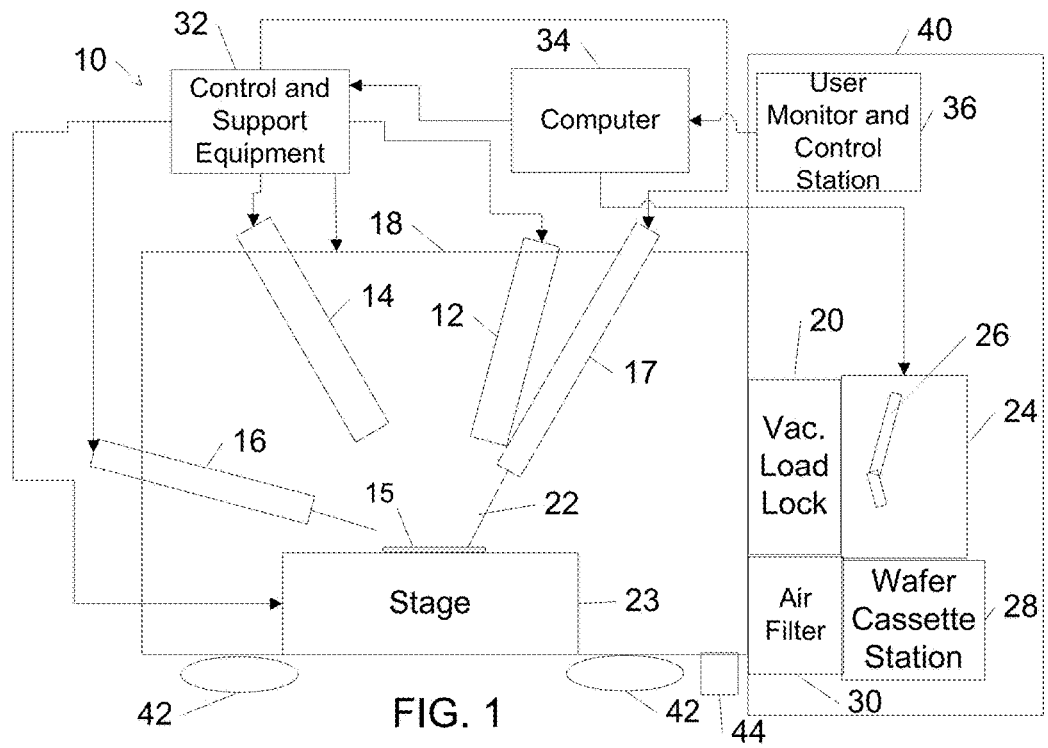
FIG. 1 shows a block diagram of a prior art nanomachining device.
Figure 2:
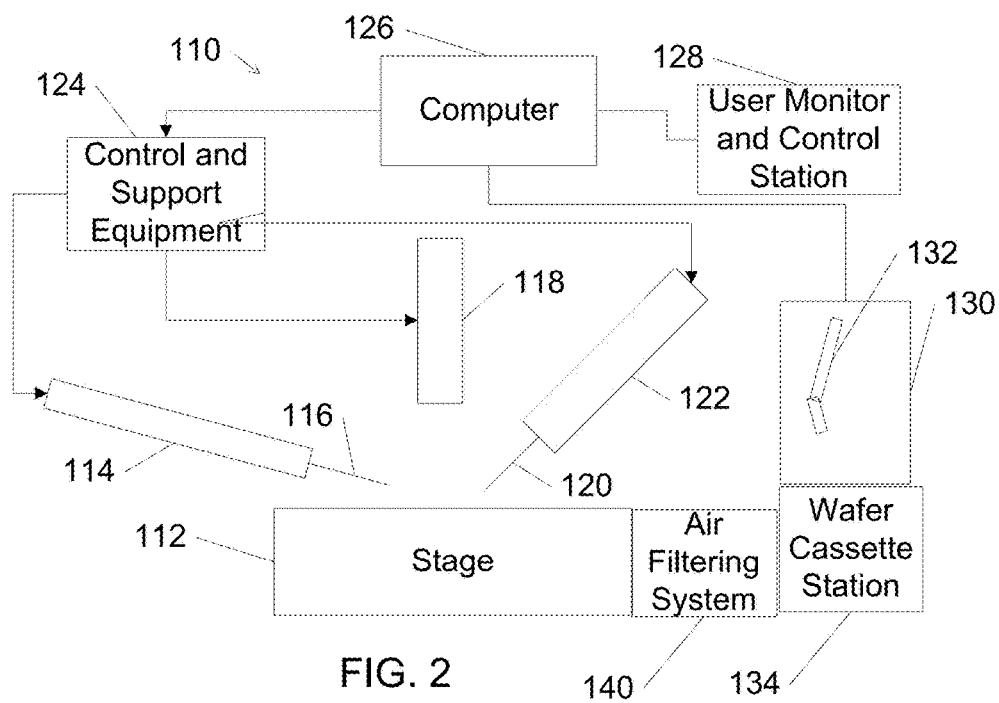
FIG. 2 shows a block diagram of a prior art ex situ lamellae plucker
Figure 3:
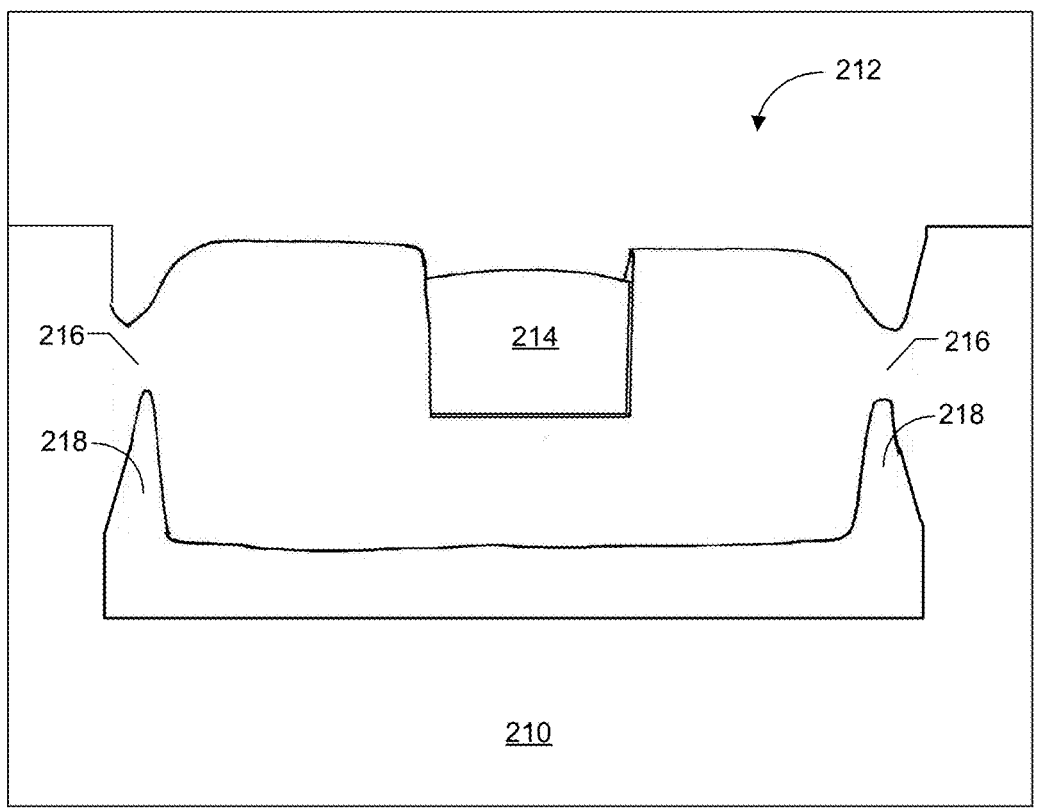
FIG. 3 shows a greatly expanded front view of a prior art lamella, formed from and still attached to wafer substrate.
Figure 4:
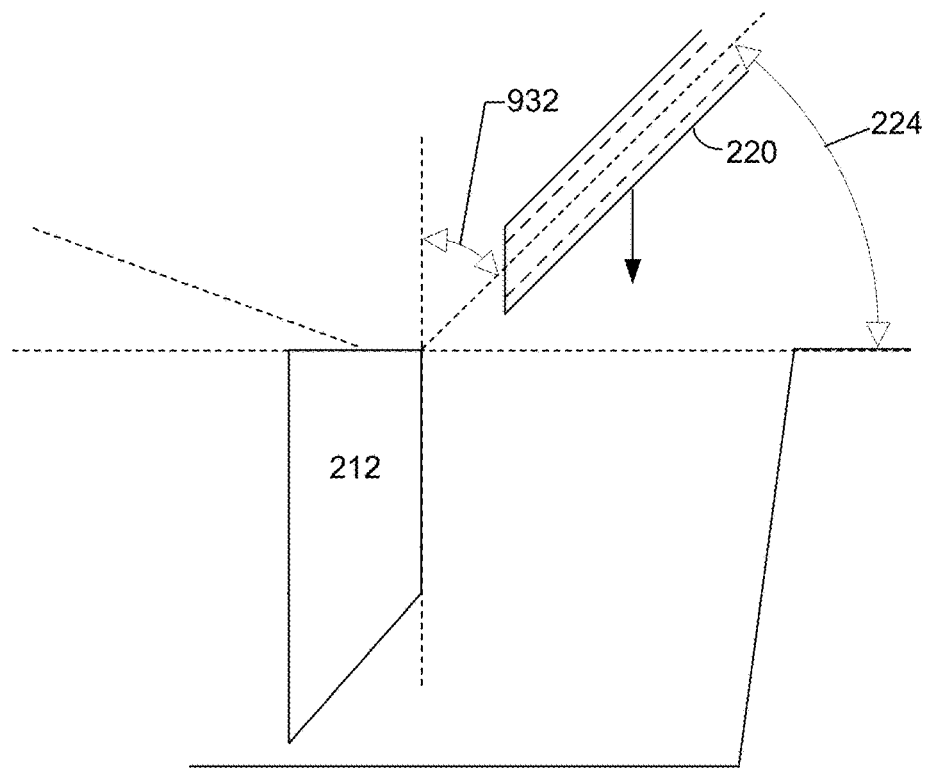
FIG. 4 shows a greatly expanded side view of the lamella of FIG. 1, in an ex situ plucker, being approached by a vacuum shaft.
Figure 5:
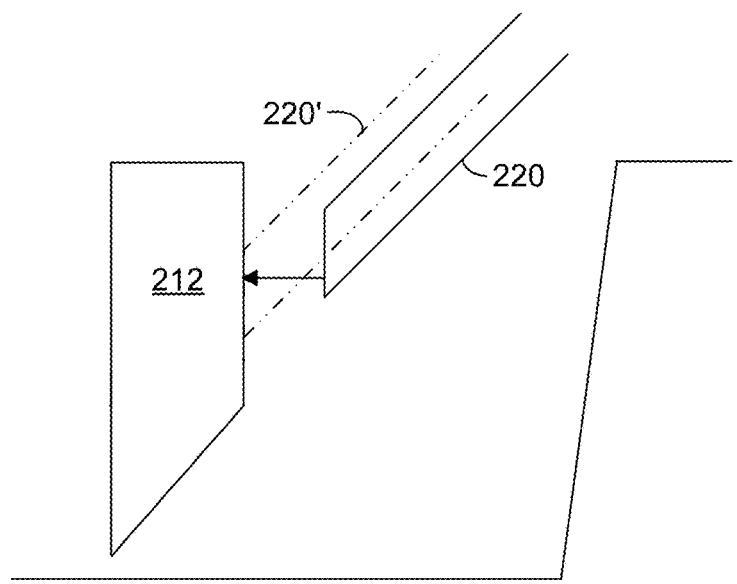
FIG. 5 shows the environment of FIG. 2, with the vacuum shaft making a final approach to the lamella.
Figure 6:
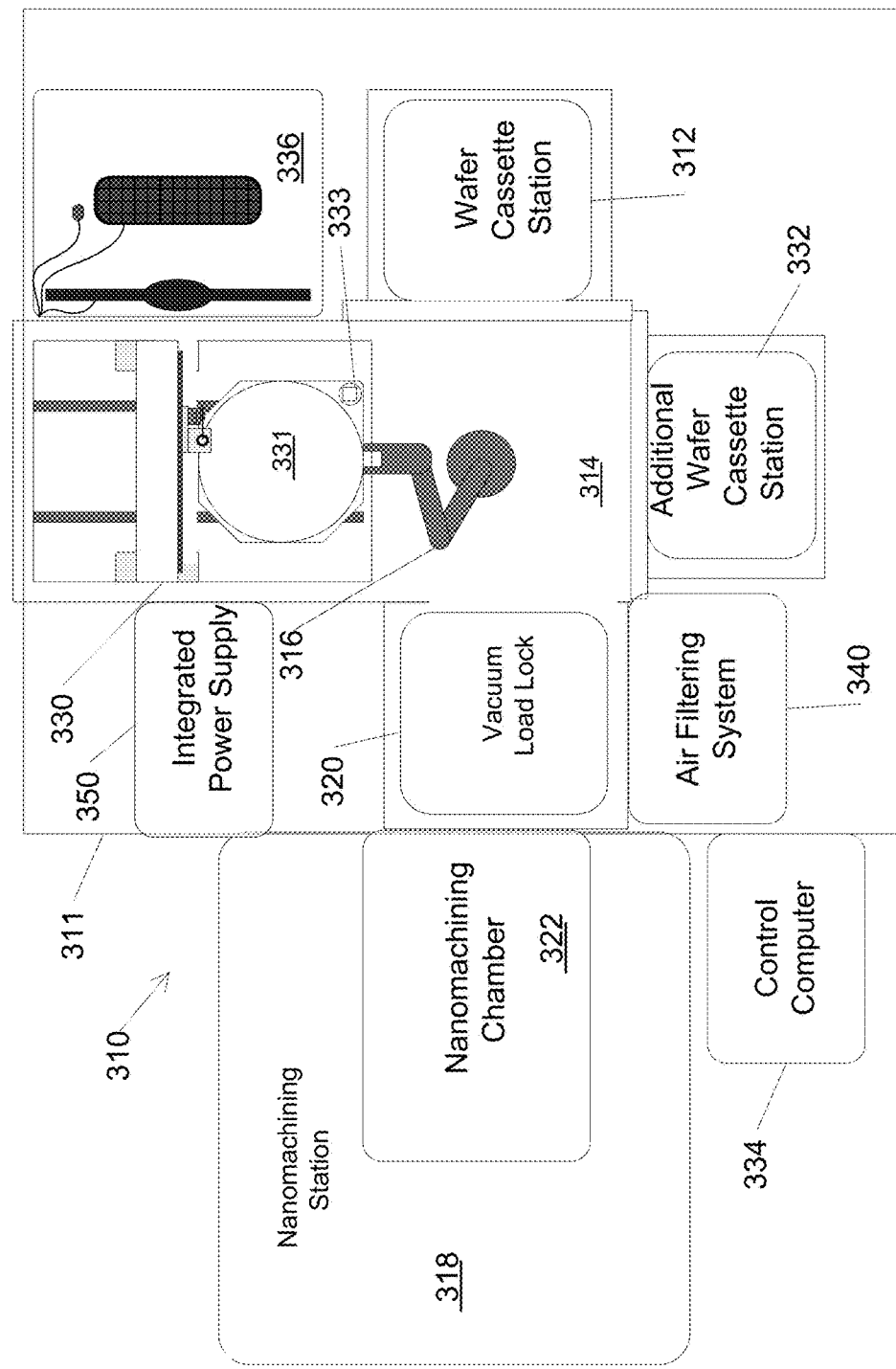
FIG. 6 is a plan view of an integrated lamellae producing station.

A preferred embodiment of the invention shown in FIG. 6 may take the form of an integrated lamellae extraction station 310 for producing lamellae from a patterned semiconductor wafer, and which has a front end 311 that includes a wafer cassette holder 312, for loading wafers into and out of station 310, a wafer transfer module 314, incorporating a robot arm 316, and a vacuum lock port 320. A lamellae plucker 330, similar to device 110 and shown holding a wafer 331, is also part of front end 311. Plucked lamellae are deposited in a holding grid 333, which is designed so that it can be moved to and used by nanomachining station 318. Optionally, front end 311 may include a second wafer cassette holder 332. A nanomachining device 318, similar to device 10, includes a nanomachining vacuum chamber 322, which is rigidly connected to the vacuum lock port. A vibration isolation and alignment system (not shown) similar to elements 42 and 44 of prior art system 10, performs the functions of vibration isolation and alignment between port 320 and the rest of front end 311.

Actions of integrated station 310 are coordinated by a control computer 334 which is connected to the different parts of device 310 by data lines (not shown). Computer 334 includes non-transitory computer readable memory media, having a program which when implemented on computer 334 executes the steps of process 410 (FIG. 7), which are described below. A user monitor and data input device 336 is connected to computer 334 by data lines (not shown), and is both fed by and controls computer 334. In one preferred embodiment device 336 includes a user station to control nanomachining device 318 and a separate station to control plucker device 330, so that two users may use device 336 simultaneously, one user control device 318 and the other controlling device 330. Air filtering system 340 maintains air cleanness in plucker 330 and wafer transfer module 314. Station 310 includes an integrated power supply 350, combining power supply functions that are separate in micromachining device 10 and plucker 110, and that are susceptible to being combined. The plucker 330 is optionally positioned on a vibration isolation table that is positioned within and support by front end 311. In such embodiments, the front end 311 supports a vibration isolation table for the plucker 330, while interfacing with nanomachining station 318 which includes its own vibration isolation station.

Figure 7:
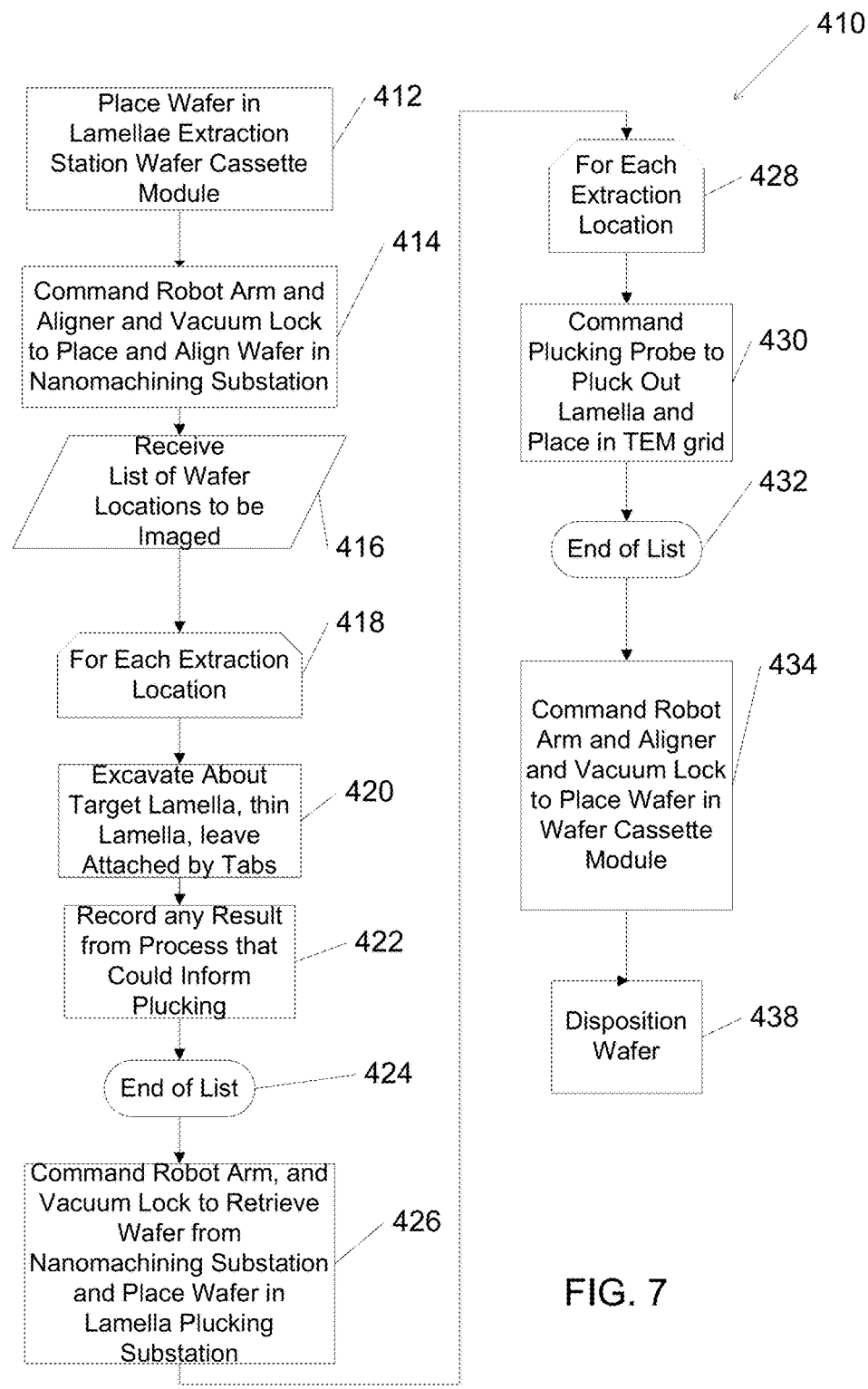
FIG. 7 is a flow diagram of lamellae production on the station of FIG. 6.

Referring to FIG. 7, in broad overview of the method of use (steps 410) of device 310, a wafer cassette is first placed in the wafer cassette holder 312 (step 412) and then the robot arm 16 and the vacuum lock port 320 are ordered (step 414) to cooperate in the placement of the resident wafer into the nanomachining chamber 322. Contemporaneously a set of one or more target lamellae locations is loaded into the computer 334 (data step 416), either through the user station, or by way of an additional data port of computer 334, such as an Ethernet connection or a USB port, and the nanomachining device 318, for each location (do while loop defined by beginning 418 and end 424) is commanded to machine into wafer 331 to create a lamella, preferably connected by tabs to the wafer (step 420). In one embodiment, control is turned over to user monitor and data input device 336, to permit a human operator to machine out a lamellae. During this process or directly afterward, data may be collected for later reference (422), including SEM or FIB imagery of the wafer, lamellae, and site from which the lamellae was formed and data derived from these images. Also, position, alignment, and orientation data of wafer 331 during machining as well as metrics of lamellae quality and success or failure in lamellae creation can be collected. A scanning electron microscope image may be formed of the lamella site, showing any anomaly, for later reference (422).

After the lamellae are formed, the computer commands the vacuum lock port 320 and the robot arm 316 to retrieve the wafer from nanomachining device 318 and place and align the wafer in lamellae plucker 330 (step 426). The lamellae plucker 330 then, for each lamella location (loop from start block 428 to finish block 432) separates the lamellae and places them in a grid for transport to a S/TEM for imaging (step 430). The data collected in step 422 may be used during this process, to avoid attempting to separate an ill-formed or accidentally detached lamellae. In one preferred embodiment, the process is automatic, but in another embodiment there is some human assistance.

The computer then commands the robot arm to retrieve the wafer from the lamellae plucker 330 and place it back in the wafer cassette holder 312 (step 434) where it is held for further disposition. If not, the wafer is dipositioned, either back into the manufacturing line, for further research, or back to the nanomachining station, if indicated by the S/TEM analysis of the lamellae, as the circumstances warrant (step 438).

The integrated lamellae extraction device 310 offers many advantages over prior art configurations. First, only one front end 311, into which a plucker station 330 is incorporated, is necessary for the entire device 310, as opposed to having a front end for both a nanomachining device and an entirely separate lamellae plucker. Also, a single air filtration system 340 is used for device 310, as opposed to two separate systems for two separate devices. Also, a single control computer 334 permits a more effortlessly complete sharing of data between nanomachining device 318 and lamellae plucker 330. Finally, integrated power supply 350 avoids the duplication inherent in two separate power supplies. Providing a plucker 330 in the front end of device 310 lowers costs, speeds throughput and eases the task load of personnel, who would otherwise have to move wafers between separate station.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim:

1. A method of creating and removing a lamella from a semiconductor wafer, comprising:
   a. providing an integrated lamellae extraction station, including:
      i. one or more wafer cassette holder, bearing a semiconductor wafer;
      ii. a wafer transfer device;
      iii. a nanomachining device, including a focused ion beam, and a nanomachining chamber, maintained in a vacuum state during nanomachining device use and a vacuum load lock for accessing said chamber;
      iv. a lamella plucker device including a micromanipulator adapted in size and function for plucking a transmission electron microscope lamella from a semiconductor wafer;
      v. a user monitor and data input device; and
      vi. a computer, including a data input assembly connected to said user monitor and data input device, and adapted to control said wafer transfer device and said plucker device, commanding said plucker device to remove lamellae at a set of locations received by way of said data input assembly;
      vii. a plucked lamellae holding device;
   b. using said wafer transfer device to transfer said wafer from said wafer cassette holder to said nanomachining device;
   c. using the nanomachining device to machine a transmission electron microscope lamella;
   d. using said wafer transfer device to transfer said wafer to said lamella plucker device;
   e. using said micromanipulator of said lamella plucker device to pluck said lamella and place it in said plucked lamellae holding device; and
   f. using said wafer transfer device to move said wafer to one of said one or more wafer cassette holders.

2. The method of claim 1, wherein said station includes a first wafer cassette holder and a second wafer cassette holder and wherein said wafer is originally in said first wafer cassette holder and is moved into said second wafer cassette holder from said plucker device.

3. The method of claim 1, performed by exclusively by a computer, which controls both said nanomachining device and said plucker device.

4. The method of claim 1, performed by a computer but with human assist to machine the lamella.

5. The method of claim 1, performed by a computer but with human assist to pluck said lamella.

6. The method of claim 1, further comprising using said nanomachining device to machine additional lamellae from said wafer, and using said micromanipulator of said lamella plucker device to pluck said additional lamellae and place them in said plucked lamellae holding device.

7. The method of claim 1, wherein said wafer transport device includes a robot arm.

8. The method of claim 1, wherein said user monitor and data input device includes a first user station for monitoring and control of the nanomachining device and a second user station for control of the plucker device.

9. The method of claim 8, wherein a first user controls the nanomachining device for an additional wafer, while a second user controls the plucking of the lamellae of claim 1.

10. The method of claim 1, wherein said nanomachining station also includes a scanning electron microscope.

11. The method of claim 1, wherein said data input assembly includes at least one data port other than said connection to said user monitor and data input device.

12. Nontransitory computer readable memory media, having a program, which when implemented on a computer, having a data input assembly and connected to control an integrated lamellae extraction station that includes one or more wafer cassette holders, at least one of which bears a semiconductor wafer; a wafer transfer device; a nanomachining device having nanomachining chamber that has a vacuum load lock; a lamellae plucker device including a micromanipulator adapted in size and function for plucking a transmission electron microscope lamella from a semiconductor wafer; and a user input and control device, communicatively connected to said data input assembly performs the following control actions:
  a. command said wafer transfer device to transfer said wafer from said wafer cassette holder to said vacuum load lock and from said vacuum load lock to said nanomachining device;
  b. receive a list of prospective lamellae sites by way of said data input assembly;
  c. command machining of transmission electron microscope lamellae;
  d. command said wafer transfer device to transfer said wafer to said plucker device;
  e. command said lamellae plucker device to pluck said lamellae and place it in said plucked lamellae holding apparatus; and
  f. command said wafer transfer device to move said wafer to one of said wafer cassette holders.

13. The memory media of claim 12 wherein said commanding of machining of lamellae includes turning control over to said user input and control device, to permit a human operator to machine said lamellae.

14. The memory media of claim 12, wherein said data input assembly includes at least one additional data port for receiving data and said list of sites does not come from said user input and control device.

15. An integrated station for extracting specimens suitable for viewing by a transmission electron microscope from a patterned semiconductor wafer, comprising:
  a. a wafer cassette holder;
  b. a wafer transfer device;
  c. a nanomachining device, including a scanning electron microscope and a focused ion beam, a vacuum load lock and an operator control device, and wherein said operator control device notes locations of created lamellae;
  d. a lamella plucker device including a micromanipulator adapted in size and function for plucking a transmission electron microscope lamella from a semiconductor wafer;
  e. a control computer, including a data input assembly and adapted to control said wafer transfer device and said lamella plucker device, commanding said lamella plucker device to remove lamellae at a set of locations received through said data input assembly;
  f. a user monitor and data input device, communicatively coupled to the computer at said data input assembly; and
  g. wherein said wafer transfer device can transfer wafers from said wafer cassette holder to said vacuum load lock; from said vacuum load lock to said lamella plucker device and from said lamella plucker device to said wafer cassette holder.

16. The station of claim 15, wherein said station includes a first wafer cassette holder and a second wafer cassette holder and wherein said wafer is originally in said first wafer cassette holder and is moved into said second wafer cassette holder from said lamella plucker device.

17. The station of claim 15, wherein said wafer transport device includes a robot arm.

18. The station of claim 15, further including an air filtering system.

19. The station of claim 15, wherein said user monitor and data input device includes a first user station for monitoring and control of the nanomachining device and a second user station for control of the lamella plucker device.

20. The station of claim 15 including an integrated power supply.

21. The station of claim 15 wherein said data input assembly includes at least one data port in addition to said connection to said user monitor and data input device.

22. The station of claim 15 wherein the lamella plucker device is positioned on a vibration isolation table.

* * * * *